(12) United States Patent
Herzinger

(10) Patent No.: US 8,564,777 B1
(45) Date of Patent: *Oct. 22, 2013

(54) SYSTEM AND METHOD FOR COMPENSATING DETECTOR NON-IDEALITIES

(75) Inventor: Craig M Herzinger, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 275 days.

This patent is subject to a terminal disclaimer.

(21) Appl. No.: 13/136,839

(22) Filed: Aug. 13, 2011

Related U.S. Application Data

(60) Provisional application No. 61/401,575, filed on Aug. 16, 2010.

(51) Int. Cl.
*G01J 4/00* (2006.01)

(52) U.S. Cl.
USPC .......................................................... 356/359

(58) Field of Classification Search
USPC .......................................................... 356/369
See application file for complete search history.

(56) References Cited

U.S. PATENT DOCUMENTS

| | | | |
|---|---|---|---|
| 4,210,401 A | 7/1980 | Batten | 356/369 |
| 4,332,476 A | 6/1982 | Stenberg et al. | 356/369 |
| 4,355,903 A | 10/1982 | Sandercock | 356/632 |
| 4,373,817 A | 2/1983 | Coates | 356/636 |
| 4,647,207 A | 3/1987 | Bjork et al. | 356/369 |
| 4,750,822 A | 6/1988 | Rosencwaig et al. | 356/445 |
| 4,826,321 A | 5/1989 | Coates et al. | 356/492 |
| 4,838,695 A | 6/1989 | Mansuripur et al. | 356/369 |
| 5,042,951 A | 8/1991 | Gold et al. | 356/369 |
| 5,045,704 A | 9/1991 | Coates | 250/372 |
| 5,329,357 A * | 7/1994 | Bernoux et al. | 356/369 |
| RE34,783 E | 11/1994 | Coates | 250/372 |
| 5,373,359 A | 12/1994 | Woollam et al. | 356/328 |
| 5,452,091 A | 9/1995 | Johnson | 356/445 |
| 5,504,582 A | 4/1996 | Johs et al. | 356/369 |
| 5,521,706 A | 5/1996 | Green et al. | 356/369 |
| 5,596,406 A | 1/1997 | Rosencwaig et al. | 356/327 |
| 5,666,201 A | 9/1997 | Johs et al. | 356/369 |
| 5,706,212 A | 1/1998 | Thompson et al. | 702/85 |
| 5,757,494 A | 5/1998 | Green et al. | 356/369 |
| 5,872,630 A | 2/1999 | Johs et al. | 356/369 |
| 5,946,098 A | 8/1999 | Johs et al. | 356/369 |
| 5,956,145 A | 9/1999 | Green et al. | 356/364 |
| 5,963,327 A | 10/1999 | He et al. | 356/369 |
| 6,084,675 A | 7/2000 | Herzinger et al. | 356/369 |
| 6,137,618 A | 10/2000 | Herzinger | 359/245 |
| 6,590,655 B2 | 7/2003 | Welch et al. | 356/369 |
| 6,795,184 B1 * | 9/2004 | Herzinger et al. | 356/369 |

* cited by examiner

*Primary Examiner* — Roy M Punnoose
(74) *Attorney, Agent, or Firm* — James D. Welch

(57) ABSTRACT

Compensating for imperfections in electromagnetic radiation detectors, and more particularly to a system and method for compensating for polarization state sensitivity and/or beam non-uniformity or the like with application in spectroscopic ellipsometers and polarimeters.

27 Claims, 4 Drawing Sheets

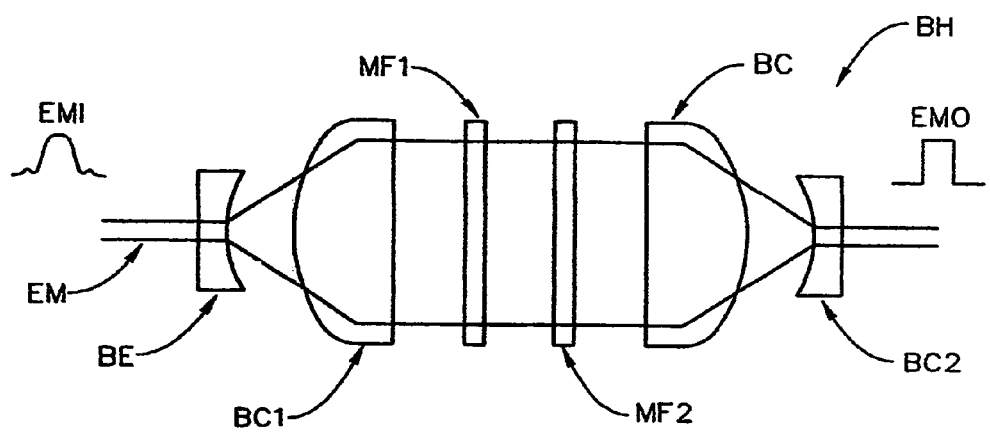
FIG. 6a
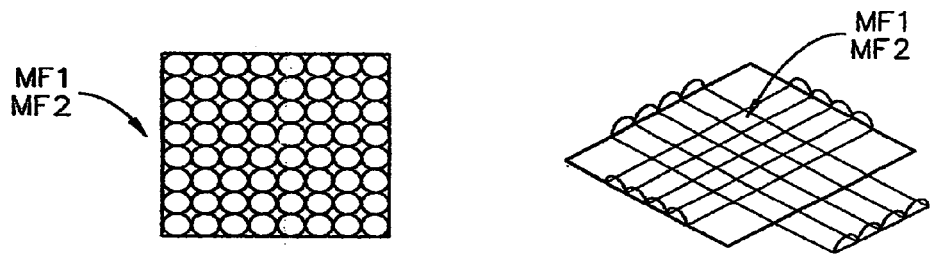
FIG. 6b
FIG. 6c
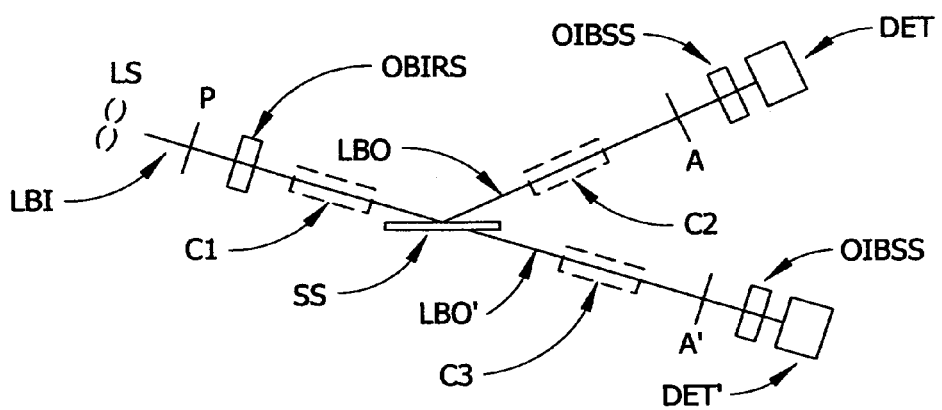
FIG. 6d

SYSTEM AND METHOD FOR COMPENSATING DETECTOR NON-IDEALITIES

This application Claims benefit of Provisional Application 61/401,575 Filed Aug. 16, 2010.

TECHNICAL FIELD

The present invention relates to compensating for imperfections in electromagnetic radiation detectors, and more particularly to a system and method for compensating for detector polarization state sensitivity and/or beam non-uniformity or the like.

BACKGROUND

Ellipsometry Basics

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

Before proceeding, as it is relevant to the present invention, it is noted that ellipsometer systems generally comprise means for setting a linear or elliptical polarization state, (typically substantially linear).

Continuing, in general, modern practice of ellipsometry typically involves causing a spectroscopic beam of electromagnetic radiation, in a known state of polarization, to interact with a sample system at at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$$\rho = rp/rs = \text{Tan}(\Psi)\exp(i\Delta)$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

| | |
|---|---|
| a. | a Source of a beam electromagnetic radiation; |
| b. | a Polarizer element; |
| c. | optionally a compensator element; |
| d. | (additional element(s)); |
| e. | a sample system; |
| f. | (additional element(s)); |
| g. | optionally a compensator element; |
| h. | an Analyzer element; and |
| i. | a Spectroscopic Detector System. |

Each of said components b.-i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. It is noted, that nulling ellipsometers also exist in which elements therein are rotatable in use, rather than rotating. Generally, use of a nulling ellipsometer system involves imposing a substantially linear polarization state on a beam of electromagnetic radiation with a linear polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow calibration of ellipsometers and evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Detector Imperfection Based Problems

It is further noted that the problem of detectors of electromagnetic radiation demonstrating sensitivity to polarization state of an electromagentic beam entered thereinto is well known. Specifically, commercially available detectors, as opposed to ideal detectors, often produce output signals which depend on the orientation of a linear polarization state of a beam entered thereinto. Patents to Green et al. U.S. Pat. Nos. 5,521,706 and 5,373,359 teach applying a compensator after a Rotating Analyzer in a Rotating Analyzer Ellipsometer system, to convert a linear polarization state to a circular polarization state before it enters a detector thereof. This serves to reduce the effects of imperfect detector characteristics that are observable in that different detector output signals develop for different orientations of the same beam polarization state exiting the rotating analyzer. Another patent, U.S. Pat. No. 6,590,655 to Welch et al., describes use of a beam homogenizing system to provide a substantially uniform beam energy profile over its width. This patent discloses that when a beam of electromagnetic radiation with a substantially homogenous energy profile is applied to a detector thereof, the effect of the polarization state of a beam entering the energy profile homogenzing system prior to the detector, is substantially eliminated. Another patent, which on its surface seems to have nothing to do with the problem, is No. 6,795,184 to Herzinger et al.

Insight from U.S. Pat. No. 6,795,184

With the present invention in mind, it is disclosed that the 184 Patent describes an Odd Bounce Image Rotation System which serves to rotate a beam image. Said 184 Patent discloses an "odd bounce optical image rotating system", and method of its application in ellipsometer and polarimeter and the like systems. The odd bounce optical image rotating system serves to rotate the azimuthal angle of a linearly, or partially linearly polarized beam of electromagnetic radiation without entering significant deviation or displacement of the propagation direction locus thereof, or significantly altering the polarization state thereof, (ie. it does not cause significant shifting of energy from a major intensity orthogonal component into the other orthogonal component, or the shifting of phase angle therebetween). The odd bounce optical image rotating system can be described as a sequence of an odd number of reflective elements oriented in a manner which causes an entering beam of electromagnetic radiation to reflect from a first thereof onto the second thereof and from the second thereof onto the third thereof etc. For a three (3) reflective element odd bounce optical image rotating element system, said three reflections cause a beam of electromagnetic radiation to emerge from the third reflective element with a rotated linear or partially linear polarization azimuthal angle and in a direction which is not significantly deviated or displaced from the locus of the input beam, even when the odd bounce optical image rotating system is caused to stepwise or continuously rotate about an axis coincident with the locus of the beam of electromagnetic radiation. The same is generally true for an odd bounce optical image rotating element system comprising any odd number, (eg. 3, 5, 7 etc.) of reflective elements. It is noted that the greater the number of reflective elements the more normal the angle of incidence a beam can make thereto, and higher angles of incidence cause less aberration effects. Also, where more than three reflection elements are present certain non-idealities caused by the reflection elements can be canceled by utilizing non-coincident coordinate systems for said reflections. A trade-off, however, is that the greater the number of reflective elements present, the more difficult it is to align the system to avoid said beam deviation and displacement.

Coupling the odd bounce optical image rotating system with a substantially linear polarizing polarizer, such as the output of a Rotating Analyzer, provides a polarizer system in which the substantially linear polarizing polarizer can remain stationary while the azimuthal angle of a substantially linearly polarized beam of electromagnetism exiting therefrom, (as viewed from a position along the locus of an electromagnetic beam caused to enter thereto), is rotated.

For general insight, it is also noted that a single three-hundred-sixty (360) degree rotation of an odd bounce optical image rotating element system about an axis coincident with a beam of electromagnetic radiation which functionally passes therethrough, causes seven-hundred-twenty (720) degrees of rotation of the major intensity orthogonal component. This is not of any critical consequence, but is mentioned as it must be taken into account during practice of methodology.

In the context of a material system investigation system, (eg. ellipsometer, polarimeter etc.), sequentially comprising:
 source of electromagnetic radiation;
 substantially linear polarizer;
 stage for supporting a sample system
 analyzer; and
 detector;
the 184 Patent teaches the presence of at least one odd bounce optical image rotating system being present between said substantially linear polarizer and said stage for supporting a sample system and/or between said stage for supporting a sample system and said analyzer, said at least one odd bounce optical image rotating system comprising an odd number of at least three reflective elements; such that a beam of electromagnetic radiation provided by said source of electromagnetic-radiation, after passing through said substantially linear polarizer, interacts with a sample system place on the stage for supporting a sample system passes through said analyzer before entering said detector, said beam of electromagnetic radiation further interacting with each of said odd number of reflective elements of said at least one odd bounce optical image rotating element, and exiting therefrom along a substantially non-deviated non-displaced trajectory.

Again, the odd bounce optical image rotating system can consist of any odd number of reflective elements, with three (3) and five (5) being preferred in the practical sense.

The 184 Patent invention also includes a method of obtaining data, comprising the steps of:
 a. providing a system which comprises an odd bounce optical image rotating system, as described above;
 b. causing a beam of electromagnetic radiation to exit said source of electromagnetic radiation, interact with said substantially linear polarizer, a sample system and said analyzer prior to entering said detector, and in addition interact with said at least one odd bounce optical image rotating element without significant change in trajectory;
 c. collecting output signals from said detector.

An additional step can further comprise the step of causing the at least one odd bounce optical image rotating element to rotate, step-wise or continuously, around the locus of the trajectory of the electromagnetic beam while practicing step c. Note, where the rotation is step-wise, motion is stopped during data acquisition.

In addition, said material system investigation system, (eg. ellipsometer, polarimeter etc.), can be caused to include a rotating compensator which during use in collecting data is caused to continuously rotate about a locus of an electromagnetic beam passing therethrough, while the substantially linear polarizer and analyzer are held essentially fixed in position and the 184 Patent odd bounce optical image rotating element is caused to be stepped through a series of rotation positions around the locus of the beam of electromagnetic radiation caused to pass therethrough, (and held motionless during data acquisition). This allows collecting data at multiple substantially linear polarization state azimuthal angle orientations, much as is typically effected by stepwise rotating a linear polarizer, (or analyzer). The benefit involved is that, especially in ellipsometer/polarimeter etc. systems which operate in the IR range of wavelengths, it can be difficult to cause rotation of a linear polarizer, (or analyzer), without adversely causing deviation of a beam of electromagnetic radiation caused to pass therethrough, or causing miscoordination of multiple elements thereof, (ie. multiple tipped wire linear polarizer as described in U.S. Pat. No. 5,946,098). The 184 Patent allows setting fixed substantially linear polarizer, and analyzer azimuthal orientations, and use the odd bounce optical image rotating element instead to effect different electromagnetic beam azimuthal rotation orientations.

Continuing, as mentioned, the 184 Patent system finds use in a spectroscopic ellipsometer system basically comprising:
 a source of polychromatic electromagnetic radiation;
 a substantially linear polarizer which is fixed in position during data acquisition;
 a stage for supporting a sample system;
 an analyzer which is fixed in position during data acquisition; and
 a multi-element spectroscopic detector system.
wherein the substantially linear polarizer and analyzer can be elements which include a birefringent element therein, through which a beam of random polarization state electromagnetic radiation is caused to pass, to the end that it emerges therefrom as a beam of electromagnetic radiation with a linear polarization imposed thereupon. Further, the substantially linear Polarizer can be a Brewster Angle element in which only a "p" or "s" component of a beam of electromagnetic radiation caused to interact therewith near a "Brewster Angle" Angle-of-Incidence, emerges therefrom in reflection or transmission, respectively; wherein the "p" component indicates a polarization state aligned with a perpendicular to a surface of a Brewster Angle Polarizer and also in the plane of incidence of said beam, and where "s" indicates a polarization components perpendicular to the "p" component and also parallel to said surface of the Brewster Angle Polarizer". While such spectroscopic ellipsometer system can be operated with a continuously rotating polarizer or analyzer during data collection, the preferred approach is to include at least one compensator somewhere between the polarizer and analyzer which is caused to continuously rotate during data acquisition, while the polarizer and analyzer are held essentially fixed.

A basic 184 Patent system then, was described in the 184 Patent as comprising a functional combination of a fixed position substantially linear polarizer in combination with an odd bounce optical image rotating system comprising a sequence of an odd number of reflective elements oriented in a manner which causes an entering beam of electromagnetic radiation to reflect from a first thereof onto the second thereof and from the second thereof onto the third thereof etc., such that said odd number of reflections cause a beam of electromagnetic radiation to emerge from the last odd number reflective element which is not significantly deviated or displaced from the locus of the input beam, even when the odd bounce optical image rotating element system is caused to rotate about an axis coincident with the locus of the beam of electromagnetic radiation. Said combination of substantially linear polarizer and odd bounce optical image rotating system serve to provide means for rotating the azimuthal angle of a substantially linearly polarized beam of electromagnetic radiation exiting said substantially linear polarizer without rotating the polarizer. Said combination of substantially linear polarizer and odd bounce optical image rotating system finds application in ellipsometer and polarimeter and the like systems.

A basic 184 Patent invention method of effecting and changing a polarization state of a beam of electromagnetic radiation comprises the steps of:
 a. providing a system for effecting a polarization state change comprising in functional combination:
  a fixed position polarizer; and
  an odd bounce optical image rotating system comprising a sequence of an odd number of reflective elements oriented in a manner which causes an entering beam of electromagnetic radiation to reflect from a first thereof onto the second thereof and from the second thereof onto the third thereof etc., such that said odd number of reflections cause a beam of electromagnetic radiation to emerge from the last reflective element thereof which is not significantly deviated or displaced from the locus of the input beam, even when the odd bounce optical image rotating element system is caused to rotate about an axis coincident with the locus of the beam of electromagnetic radiation;
 b. entering an electromagnetic beam to said polarizer;
 c. stepwise or continuously rotating said odd bounce optical image rotating system about an axis coincident with the locus of the electromagnetic beam.
Said method of effecting and changing a polarization state of a beam of electromagnetic radiation preferably involves the odd bounce optical image rotating system being stepwise rotated about the axis coincident with the locus of the electromagnetic beam such that the polarization state of said beam of electromagnetic radiation is generally affected much as would be the case if the polarizer were so stepwise rotated.

Where data is to be obtained by directing a resulting beam into a detector, the odd bounce optical image rotating system can be caused to continuously rotate during data acquisition, however, preferred 184 Patent invention practice was to cause another element, (eg. an analyzer or compensator), to be present and rotate during data acquisition while holding the polarizer and odd bounce optical image rotating system both motionless between stepped azimuthal angle changes.

In addition to the above identified patents to Green et al. U.S. Pat. Nos. 5,521,706 and 5,373,359, U.S. Pat. No. 6,590,655 to Welch et al. U.S. Pat. No. 6,795,184 to Herzinger et al., the following patents are also disclosed:

Patent to Herzinger, U.S. Pat. No. 6,137,618 is disclosed as it describes a Single Brewster Angle Polarizer in the context of multiple reflecting means, and discloses prior art dual Brewster Angle Single Reflective Means Polarizer Systems.

Patent, to Herzinger et al., U.S. Pat. No. 6,084,675 describes an adjustable beam alignment compensator/retarder with application to spectroscopic ellipsometry.

U.S. Pat. No. 5,946,098 to Johs et al., describes dual tipped wire grid polarizers in combination with various compensator/retarder systems.

Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

Further patents of which the Inventor is aware include:
U.S. Pat. Nos. 5,757,494; and
5,956,145;
to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said patents describes the presence of a variable, transmissive, bi-refringent component which is added, and the application thereof during data acquisition to enable the identified capability.

A patent to He et al., U.S. Pat. No. 5,963,327 is disclosed as it describes an ellipsometer system which enables providing a polarized beam of electromagnetic radiation at an oblique angle-of-incidence to a sample system in a small spot area.

Patents of general interest of which the Inventor is aware include:
Patent to Woollam et al, U.S. Pat. No. 5,373,359;
Patent to Johs et al. No. 5,666,201;
Patent to Green et al., U.S. Pat. No. 5,521,706; and
Patent to Johs et al., U.S. Pat. No. 5,504,582;
and are disclosed as they pertain to ellipsometer systems.

A patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This patent also describes calibration utilizing two sample substrates, which have different depths of surface coating.

Other patents which describe use of reflected electromagnetic radiation to investigate sample systems are:
U.S. Pat. Nos. RE 34,783,
4,373,817,
5,045,704
to Coates; and
U.S. Pat. No. 5,452,091
to Johnson.

A patent to Bjork et al., U.S. Pat. No. 4,647,207 is disclosed as it describes an ellipsometer system which has provision for sequentially, individually positioning a plurality of reflective polarization state modifiers in a beam of electromagnetic radiation. U.S. Pat. Nos. 4,210,401; 4,332,476 and 4,355,903 are also identified as being cited in the 207 Patent. It is noted that systems as disclosed in these patents, (particularly in the 476 Patent), which utilize reflection from an element to modify a polarization state can, if such an element is an essential duplicate of an investigated sample and is rotated ninety degrees therefrom, the effect of the polarization state modifying element on the electromagnetic beam effect is extinguished by the sample.

A patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,596,406 are also identified as they describe systems which impinge electromagnetic beams onto sample systems at oblique angles of incidence. The 406 Patent provides for use of multiple wavelengths and multiple angles of incidence. For similar reasons U.S. Pat. No. 5,042,951 to Gold et al. is also disclosed.

In addition to the identified patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Smith, titled "An Automated Scanning Ellipsometer", Surface Science, Vol. 56, U.S. Pat. No. 1. (1976), is also mentioned as it describes an ellipsometer system which does not require any moving, (eg. rotating), elements during data acquisition.

Even in view of relevant prior art, there remains need for a convenient approach to reducing Detector Polarization State or Beam Non-Uniformity Dependence to linearly polarized beams of electromagnetic radiation. The present invention responds to said identified needs.

DISCLOSURE OF THE INVENTION

The present invention system is generally distinguished by the presence in an optical measurement system (ellipsometer, polarimeter, etc.), comprising a polarization state or image rotation or the like, or beam homogenizing system in the beam path between the detector and the last optical element needed to construct the optical measurement in the usual manner, typically an analyzer.

Detectors, or more generally detector systems (detector+optics+housing), can exhibit polarization-dependent sensitivity (PDS) or beam non-uniformity sensitivity effects whereby it appears that the responsivity of the detector system changes depending upon the polarization state or beam non-uniformity of the light impinging on the detector. For ellipsometric and polarimetric measurement systems, this is a complication that can reduce measurement accuracy and can require a more complicated calibration model.

One approach to remove such effects related to the linearly-polarized component of the light to be detected would be to rotate the detector on an axis around the incoming light beam and then average the detected signal over that rotation. Rotating the detector is usually an impractical solution. However, it is possible to use an image rotation system to rotate the incoming light beam (or at least the linearly-polarized component of the beam) around its axis. Rotating the beam in this way can accomplish the same basic averaging as rotating the detector. In fact, from an observer looking down the beam from the input-side of the image rotator, it would appear that the detector is rotating, while looking into the beam from the detector it would appear the beam is rotating. Probe beams used in optical measurement systems are not always uniform, in intensity or in polarization state, over a cross section of the beam. When a non-uniform probe beam interacts with a spatially non-uniform detector measurement artifacts can be created that can reduce measurement accuracy and can require a more complicated calibration model. One approach to average across the non-uniformities is the cause the beam to move across the detector so that to the extent possible every part of the probe beam would interact with every part of the detector active area. However, often the beam diameter and detector active areas are approximately the same size so it is impractical to move the beam or detector much in a side-to-side offset motion. It is however possible to rotate the beam or the detector about the beam axis while keeping the beam on the active area of the detector. As mentioned in the previous paragraph regarding PDS averaging, an image rotation system placed in the beam path prior to the detector would achieve the result. Furthermore, an image rotation system can also be used generate both small and large side-to-side offset of the beam relative to the detector to the extent that would be applicable in increasing the averaging of beam profile across the detector active area.

Continuing, the present invention can be an ellipsometer or polarimeter with improved detector performance comprising:
a source of electromagnetic radiation;
a polarizer;

a stage for supporting a sample system;
an analyzer;
a detector;
optionally, at least one compensator between said polarizer and analyzer; and
at least one beam modifying detector performance improving system between said analyzer and detector.

In use a beam of electromagnetic radiation provided by said source thereof passes through said polarizer and interacts with a sample system on said stage for supporting a sample system, said beam further passing through any present compensator present between said polarizer and analyzer, then passing through said analyzer and said at least one beam modifying detector performance improving system, and then into said detector.

The present invention can also be described as system for compensating detector beam non-uniformity sensitivity in a material system investigating system comprising:
a source of electromagnetic radiation;
a polarizer;
a stage for supporting a sample system;
an analyzer;
a detector;
optionally, at least one compensator between said polarizer and analyzer; and
at least one optical image beam scrambling system between said analyzer and detector.

In use a beam of electromagnetic radiation provided by said source thereof passes through said polarizer and interacts with a sample system on said stage for supporting a sample system, said beam further passing through any present compensator present between said polarizer and analyzer, then passing through said analyzer and said at least one optical image beam scrambling system, and then into said detector.

The present invention can also be described as a system for compensating detector beam polarization state sensitivity in a material system investigating system comprising:
a source of electromagnetic radiation;
a polarizer;
a stage for supporting a sample system;
an analyzer;
a detector;
optionally, at least one compensator between said polarizer and analyzer; and
at least one beam polarization state scrambling system between said analyzer and detector.

In use a beam of electromagnetic radiation provided by said source thereof passes through said polarizer and interacts with a sample system on said stage for supporting a sample system, said beam further passing through any present compensator present between said polarizer and analyzer, then passes through said analyzer and said at least one beam polarization state scrambling system, and into said detector.

In any of the foregoing systems the at least one beam modifying detector performance improving system can be selected from the group consisting of:
at least one optical image rotating system which is caused to rotate in use;
a kaleidoscope;
a fiber waveguide.

Further, the at least one beam modifying detector performance improving system can be selected to comprises an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, typically the odd bounce optical image rotating system consists of three or five reflective elements.

The at least one beam modifying detector performance improving system can be an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

A present invention method of improving detector performance in an ellipsometer or polarimeter comprises:
a) providing an ellipsometer or polarimeter system comprising:
a source of electromagnetic radiation;
at least one beam modifying detector performance improving system; and
a detector;
such that in use a beam of electromagnetic radiation provided by said source thereof, interacts with said at least one beam modifying detector performance improving system and then enters into said detector.

The method further comprises:
b) causing said source of electromagnetic radiation to direct a beam of electromagnetic radiation such that it passes through said at least one beam modifying detector performance improving system and enters said detector;
the result being that said detector receives a beam having characteristics which improve results provided thereby.

Another present invention method compensates detector beam non-uniformity sensitivity and comprises the steps of:
a) providing a system comprising:
system for compensating detector beam non-uniformity sensitivity in a material system investigating system comprising:
a source of electromagnetic radiation;
a polarizer;
a stage for supporting a sample system;
an analyzer;
a detector;
optionally, at least one compensator between said polarizer and analyzer; and
at least one optical image beam scrambling system between said analyzer and detector;
such that in use a beam of electromagnetic radiation provided by said source thereof passes through said polarizer, interacts with a sample system on said stage for supporting a sample system, said beam further passing through any present compensator present between said polarizer and analyzer, then passes through said analyzer and said at least one optical image beam scrambling system, and then into said detector.

b) causing said source of electromagnetic radiation to direct a beam of electromagnetic radiation through said polarizer, such that it interacts with said sample system on said stage for supporting a sample system, any present compensator between said polarizer and analyzer, then pass through said analyzer, through said at least one optical image beam scrambling system and enter said detector.

The step of providing a system involves providing said at least one optical image beam scrambling system in the form of at least one odd bounce optical image rotating system comprising an odd number of at least three reflective elements oriented such that a beam of electromagnetic radiation entered thereinto interacts with each of said at least three reflective elements of said at least one odd bounce optical image rotating system and exits therefrom along a non-deviated non-displaced trajectory.

Another present invention method compensates detector beam polarization state sensitivity and comprises the steps of:
a) providing a system comprising:
system for compensating detector beam polarization state sensitivity in a material system investigating system comprising:
a source of electromagnetic radiation;
a polarizer;
a stage for supporting a sample system;
an analyzer;
a detector;
optionally, at least one compensator between said polarizer and analyzer; and
at least one beam polarization state scrambling system between said analyzer and detector.
In use a beam of electromagnetic radiation provided by said source thereof passes through said polarizer, interacts with a sample system on said stage for supporting a sample system, said beam further passing through any present compensator present between said polarizer and analyzer, then passes through said analyzer and said at least one beam polarization state scrambling system, and then into said detector;
b) causing said source of electromagnetic radiation to direct a beam of electromagnetic radiation through said polarizer, such that it interacts with said sample system on said stage for supporting a sample system, and with any present compenstor between said polarizer and analyzer, then passes through said analyzer, through said at least one beam polarization state scrambling system and enters said detector.

The methodology recited above can involve the step of providing at least one optical image beam scrambling system in the form of at least one odd bounce optical image rotating system comprising an odd number of at least three reflective elements oriented such that a beam of electromagnetic radiation entered thereinto interacts with each of said at least three reflective elements of said at least one odd bounce optical image rotating system and exits therefrom along a non-deviated non-displaced trajectory.

Said methodology can also provide that said at least one optical image beam scrambling system is an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

The present invention can also be considered to be a system for homogenizing a non-uniform beam in a material system investigating system comprising:
a source of electromagnetic radiation;
at least one image scrambling system; and
a detector.
In use a beam of electromagnetic radiation provided by said source thereof, interacts with said at least one image scrambling system and then enters into said detector. The result is that said detector receives a substantially homogenous beam thereby reducing the effect of beam non-uniformity on output therefrom resulting from detector sensitivity to beam non-uniformity.

Said system can involve the at least one image scrambling system be selected from the group consisting of:
at least one image rotating system which is caused to rotate in use;
a kaleidoscope which is caused to rotate in use;
a fiber waveguide.

Where the at least one image rotating system is selected, it can comprise an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory. The odd bounce optical image rotating system consists of three reflective elements or five reflective elements.

Said system can further comprise a stage for supporting a sample such that in use said source of electromagnetic radiation causes said beam of electromagnetic radiation to interact with a sample placed on said stage, then enter said detector, and the system is a reflectometer or spectrophotometer.

Said system can alternatively further comprise, in addition to said at least one image scrambling system with which said beam interacts, a polarizer, a stage for supporting a sample and an analyzer such that in use said source of electromagnetic radiation causes said beam of electromagnetic radiation to pass through said polarizer, interact with a sample placed on said stage, then pass through said analyzer and enter said detector, said system optionally further comprising at least one compensator between said polarizer and analyzer; in which said system comprises an ellipsometer or polarimeter. In use the at least one of said polarizer, analyzer and optional at least one compensator can be caused to rotate during use. Further, the system at least one image scrambling system can be an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, which, during use, is caused to rotate with all rotating elements being synchronized and rotating at integer multiples of a selected rotation rate, such that each of said rotating elements simultaneously completes the same, or a different full integer numbers of rotations.

It is noted that any of the methods disclosed herein can further include developing signal(s) from detector output, and performing at least one selection from the group consisting of:
storing at least some data provided by said data detector in machine readable media;
analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result; and analyzing at least some of the data provided by said data detector and causing at least some thereof to produce a signal which is applied to provide a concrete and tangible result.

The present invention will be better understood by reference to the Detailed Description Section of this Specification, in combination with the Drawings.

BRIEF DESCRIPTION OF THE DRAWINGS

FIGS. 6a-6c demonstrate a beam homogenizing system (BH).

FIG. 6d shows FIG. 4 indicating addition of at least one image scrambling system between said analyzer and detector.

DETAILED DESCRIPTION

Insight from U.S. Pat. No. 6,795,184

Figure 1:
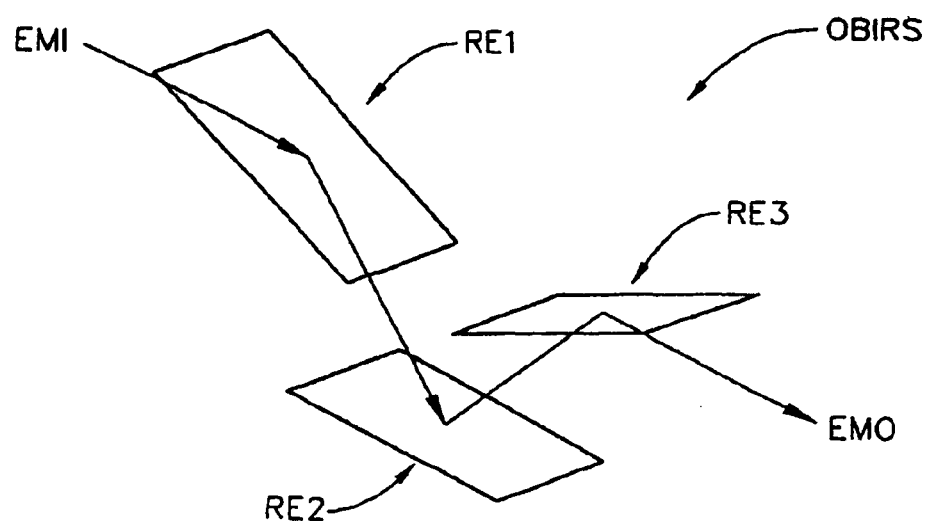
FIG. 1 demonstrates an odd bounce image rotating system comprising three (3) reflecting elements.

Turning now to FIG. 1, there is represented a three (3) bounce odd bounce image rotating system (OBIRS) comprising three (3) reflective elements (RE1), (RE2) and (RE3), oriented with respect to one another such that an input beam of electromagnetic radiation (EMI) exits as an output beam of electromagnetic radiation (EMO) without any deviation or displacement being entered into the locus thereof.

Figure 2:
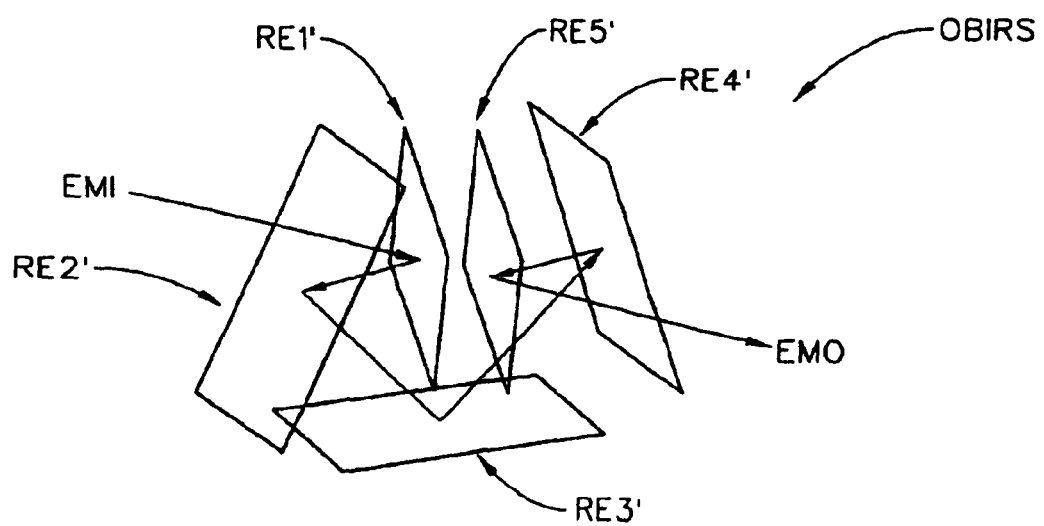
FIG. 2 demonstrates an odd bounce odd image rotating system comprising five (5) reflecting elements.

FIG. 2 demonstrates a five (5) bounce odd bounce image rotating system (OBIRS) wherein five reflective elements (RE1'), (RE2') (RE3'), (RE4') and (RE5') oriented with respect to one another such an input beam of electromagnetic radiation (EMI) exits as an output beam of electromagnetic radiation (EMO) without any deviation or displacement being entered into the locus thereof. Note generally that the angle of incidence of the (EMI) and (EMO) beams of electromagnetic radiation are nearer normal than is the case in the FIG. 1 three (3) bounce odd bounce image rotating system (OBIRS). This is beneficial in that the closer to normal the angle of incidence, the less aberration effects are entered to the beam. However, it is also to be appreciated that construction of the FIG. 2 system is more difficult than is construction of a FIG. 1 system.

Figure 3A:
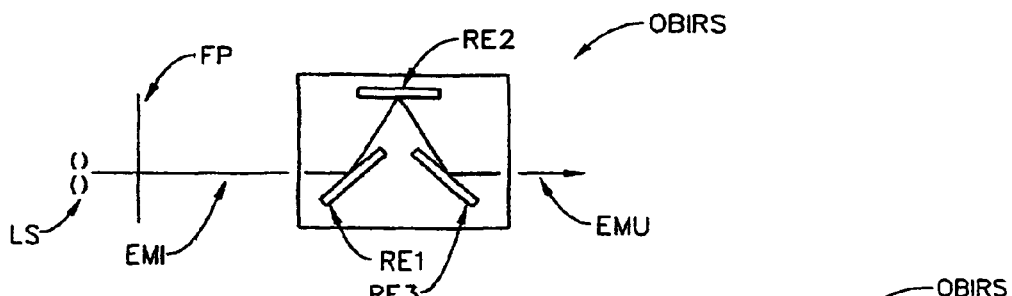
FIG. 3a demonstrates a combination fixed position polarizer and rotatable odd bounce image rotating system.

FIG. 3a demonstrates a combination fixed position polarizer (FP) and rotatable odd bounce image rotating system (OBIRS) which in combination provide a means for providing a polarized beam of electromagnetic radiation and for controlling the azimuthal angle of the polarization, without the need to rotate the fixed polarizer (FP).

Figures 3B, 3C:
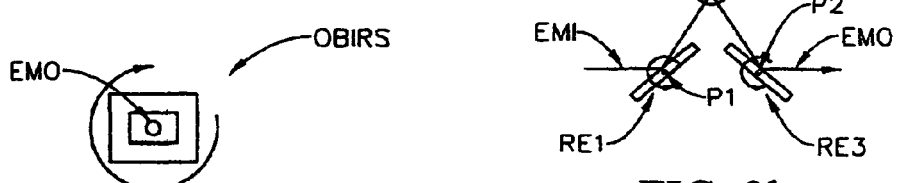
FIG. 3b shows that the reflective elements in the rotatable odd bounce image rotating system of FIG. 3a can be pivotally mounted.
FIG. 3c shows an end view of the rotatable odd bounce image rotating system of FIG. 3a is rotatable about the output electromagnetic beam.

FIG. 3b demonstrates that the reflective elements (RE1), (RE2) and (RE3) can be mounted pivotally via pivots (P1), (P2) and (P3) to allow easy alignment, so that the input (EM1) and output (EMO) beams of electromagnetic radiation can be oriented along the same locus, without deviation and displacement effects causing the output (EMO) beam to exit along a different locus than along that input beam (EMI) enters.

Figures 3D, 3E:
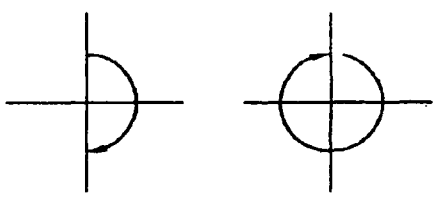
FIGS. 3d and 3e are included to demonstrate that a physical half rotation of an odd bounce optical image rotating system (OBIRS), (see FIG. 3d), around output electromagnetic beam (EMO), as viewed in FIG. 3c causes a full rotation of the linear polarization vector (see FIG. 3e).

FIGS. 3d and 3e are included to demonstrate that a physical half rotation of an odd bounce optical image rotating system (OBIRS), (see FIG. 3d), around output electromagnetic beam (EMO), as viewed in FIG. 3c causes a full rotation of the polarization vector (see FIG. 3e).

Figure 4:
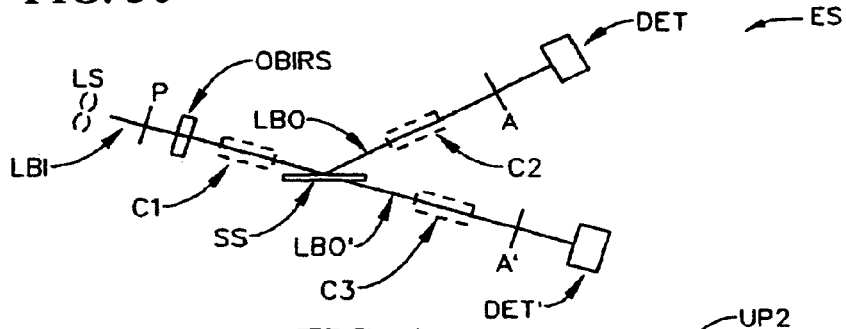
FIG. 4 demonstrates a rotating compensator ellipsometer system in which an odd bounce image rotating system is present after a fixed position linear polarizer.

FIG. 4 demonstrates a rotating compensator ellipsometer system in which an odd bounce image rotating system (OBIRS) is present immediately after a fixed polarizer (FP). Note also the relative orientation of a/polychromatic electromagnetic radiation (LB1), optional compensator (C1) sample system (SS), optional compensator (C2), analyzer (A) and detector (DET) in the demonstrative upper reflective portion, (eg. follow electromagnetic beam, (LBI) to (LBO). Further shown is a demonstrative transmissive portion comprised of optional compensator (C3), analyzer (A') and detector (DET'), (eg. follow electromagnetic beam (LBI) to (LBO). Preferred present invention practice has it that at-least one of the compensators (C1), (C2) and (C3) will be present and caused to rotate during data acquisition and the odd bounce image rotating system (OBIRS) will be stepped to various azimuthal angle positions and set motionless during data acquisition, which the fixed linear polarizer (FP) and analyzer (A) (A') are held stationary. That is, the preferred present invention application is in a rotating compensator ellipsometer system, wherein the combination of the fixed polarizer and the odd bounce image rotating system (OBIRS) provide an effective rotatable polarizer. This is useful where a polarizer, (such as tipped wire grid plate polarizers used in the IR wavelength range), is difficult to rotate while maintaining alignment of the components therein and while avoiding deviation and displacement affects between input (EMI) and output (EMO) electromagnetic beams.

Figure 5:
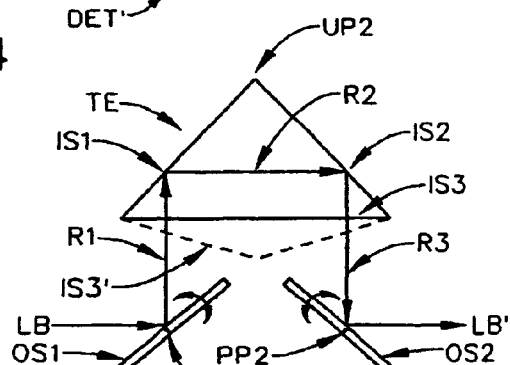
FIG. 5 demonstrates a preferred compensator (C) (C') C"), (see FIG. 4), for use in a rotating compensator ellipsometer system for application in the IR range of wavelengths.

FIG. 5 demonstrates a preferred compensator (C) (C') C") for use in a rotating compensator ellipsometer system for application in the IR range of wavelengths. The compensator system comprises, as shown in upright side elevation, first (OS1) and second (OS2) orientation adjustable mirrored elements which each have reflective surfaces. Note the adjustability enabling pivot (PP1) (PP2) mountings. Said compensator system further comprises a third element (TE) which, as viewed in upright side elevation presents with first (IS1) and second (IS2) sides which project to the left and right and downward from an upper point (UP2), said third element (TE) being made of material which provides reflective interfaces on first and second sides inside thereof. Said third element (TE) is oriented with respect to the first (OS1) and second (OS2) orientation adjustable elements such that in use an input electromagnetic beam of radiation (LB) caused to approach one of said first (OS1) and second (OS2) orientation adjustable mirrored elements along an essentially horizontally oriented locus, is caused to externally reflect therefrom upwardly vertically oriented, (see beam (R1)) then enter said third element (TE) and essentially totally internally reflect from one of said first and second sides thereof, then proceed along an essentially horizontal locus (see beam (R2)), and essentially totally internally reflect from the other of said first (OS1) and second (OS2) sides and proceed along an essentially downward vertically oriented locus, (see beam (R3)), then reflect from the other of said first (OS1) and second (OS2) adjustable mirrored elements and proceed along an essentially horizontally oriented (LB') propagation direction locus which is essentially undeviated and undisplaced from the essentially horizontally oriented locus of said input beam of electromagnetic radiation even when said compensator is caused to rotate about the locus of the beam of electromagnetic radiation, with the result being that retardation is entered between orthogonal components of said input electromagnetic beam of radiation. Also shown are third element lower side (IS3), with indication that it can be shaped as shown by (IS3'), and retain functionality.

FIGS. 6a-6c demonstrate a beam homogenizing system (BH). FIG. 6a shows a beam expander (BE), a first beam collimator (BC1), multi-faceted optical elements (MF1) (MF2), a beam condenser (BC), and a second beam collimator (BC2). FIGS. 6b and 6c show constructions of multi-faceted optical elements (MF1) (MF2). In use a beam (EM) of electromagnetic radiation is caused first beam collimator (BC1), pass through the multi-faceted optical elements (MF1) (MF2), beam condenser (BC), and second beam collimator (BC2) and exit the beam expander (BE). Note that the beam energy content profile (EMI) entering the beam expander (BE) is homogenized to that of (EMO) exiting the beam collimator (BC2).

Note that a beam homogenizing system (BH) can also be termed "a beam polarization state scrambling system."

FIG. 6d shows FIG. 4 indicating addition of at least one image scrambling system (OIBSS) between said analyzer (A) and detector (DET), as per the present invention.

New Disclosure

Figure 7A:
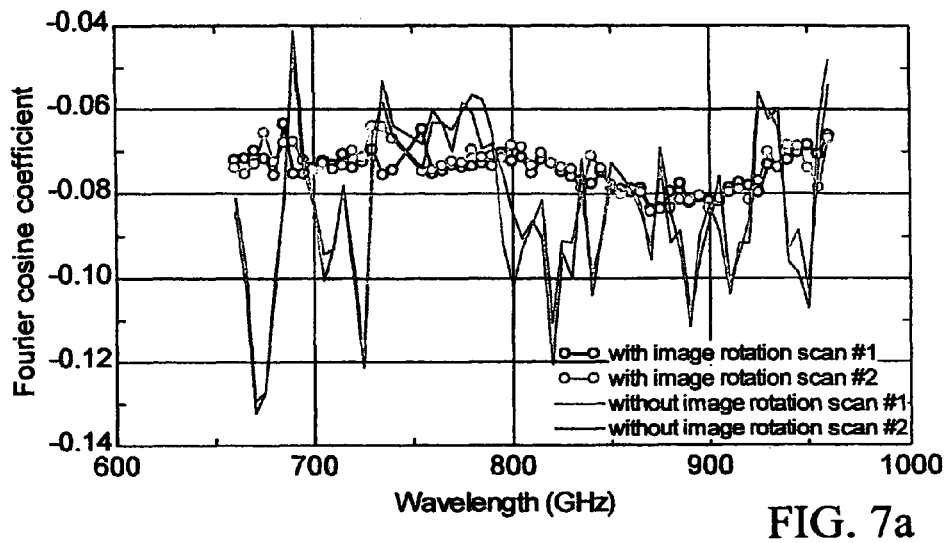
FIGS. 7a and 7b show improved Fourier Coefficient results achieved by applying the present invention methodology during data acquisition.
Figure 7B:
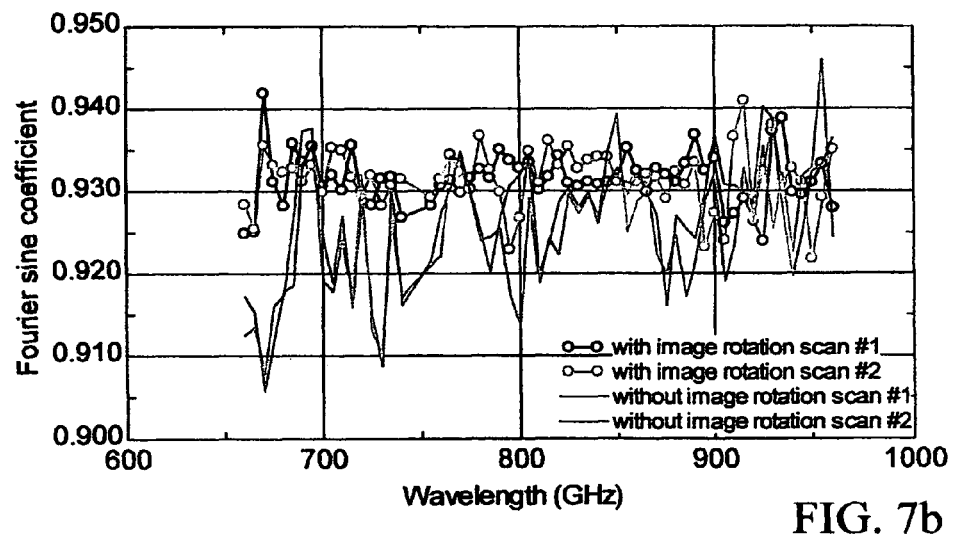

As specifically regards the present invention, FIGS. 7a and 7b demonstrate Fourier coefficient (FC) measurements made by an ellipsometer system in straight-through configuration and operating in the rotating-analyzer configuration at frequencies from 660-960 GHz, (note, said frequencies are demonstrative and not limiting). Nominally these FC measurements should not be a strong function of frequency because the polarizing elements (eg. a wire-grid polarizers) and the detector (eg. Golay cell) should not be strong functions of frequency. As shown in the graphs of FIGS. 7a and 7b, including a continuously moving image rotator located between the rotating-analyzer and the detector, and synchronized to the ellipsometer measurement to exactly average over whole rotations of the image rotation, can achieve much better FC results. Measurements of the Fourier cosine and sine terms were made with and without the image rotation between the analyzer and the detector. Each scan was done twice to demonstrate that the larger range of values without the image rotation being used represents an inaccuracy in that the values are most repeatable. With the image rotation being used, the results are a much weaker function of the frequency and therefore much closer to the nominally expected results for an air measurement and therefore much more useful in building a working spectroscopic ellipsometer system.

It is to be understood that the present invention can be realized by systems configured for application in any functional frequency/wavelength range, and applied in any functional frequency/wavelength range.

Finally, it is to be understood that while preferred embodiments provide for application of a linear polarizer, the present invention can be used with a substantially linearly polarizing polarizer, or a polarizer which provides partially linearly polarization. In the Claims the term "polarizer" should then be interpreted broadly to mean preferably a linear polarizer, but including polarizers which provide partially linearly polarization.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A system for compensating detector beam non-uniformity sensitivity in a material system investigating system comprising:
   a source of electromagnetic radiation;
   a polarizer;
   a stage for supporting a sample system;
   an analyzer;
   a detector;
   optionally, at least one compensator between said polarizer and analyzer; and
   at least one image scrambling system between said analyzer and detector;
   such that in use a beam of electromagnetic radiation provided by said source thereof passes through said polarizer and interacts with a sample system on said stage for supporting a sample system, said beam further passing through any present compensator present between said polarizer and analyzer, then passing through said analyzer and said at least one image scrambling system, and then into said detector.

2. A system as in claim 1, wherein the at least one image scrambling system is selected from the group consisting of:
   at least one optical image rotating system which is caused to rotate in use;
   a kaleidoscope;
   a fiber waveguide.

3. A system as in claim 2 in which the at least one optical image rotating system is selected and comprises an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory.

4. A system as in claim 3 in which odd bounce optical image rotating system consists of three reflective elements.

5. A system as in claim 3 in which odd bounce optical image rotating system consists of five reflective elements.

6. A system as in claim 3, in which said at least one image scrambling system is an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

7. A system as in claim 1 in which material system investigating system comprises an ellipsometer or polarimeter.

8. A method of compensating detector beam non-uniformity sensitivity comprising the steps of:
   a) providing a system comprising:
   system for compensating detector beam non-uniformity sensitivity in a material system investigating system comprising:
   a source of electromagnetic radiation;
   a polarizer;
   a stage for supporting a sample system;
   an analyzer;
   a detector;
   optionally, at least one compensator between said polarizer and analyzer; and
   at least one image scrambling system between said analyzer and detector;
   such that in use a beam of electromagnetic radiation provided by said source thereof passes through said polarizer, interacts with a sample system on said stage for supporting a sample system, said beam further passing through any present compensator present between said polarizer and analyzer, then passes through said analyzer and said at least one image scrambling system, and then into said detector;
   b) causing said source of electromagnetic radiation to direct a beam of electromagnetic radiation through said polarizer, such that it interacts with said sample system on said stage for supporting a sample system, any present compensator between said polarizer and analyzer, then pass through said analyzer, through said at least one image scrambling system and enter said detector.

9. A method as in claim 8 in which the step of providing a system involves providing said at least one image scrambling system in the form of at least one odd bounce optical image rotating system comprising an odd number of at least three reflective elements oriented such that a beam of electromagnetic radiation entered thereinto interacts with each of said at least three reflective elements of said at least one odd bounce optical image rotating system and exits therefrom along a non-deviated non-displaced trajectory.

10. A system for compensating detector beam polarization state sensitivity in a material system investigating system comprising:
   a source of electromagnetic radiation;
   a polarizer;
   a stage for supporting a sample system;
   an analyzer;
   a detector;
   optionally, at least one compensator between said polarizer and analyzer; and
   at least one beam polarization state scrambling system between said analyzer and detector;
   such that in use a beam of electromagnetic radiation provided by said source thereof passes through said polarizer and interacts with a sample system on said stage for supporting a sample system, said beam further passing through any present compensator present between said polarizer and analyzer, then passes through said analyzer and said at least one beam polarization state scrambling system, and into said detector.

11. A system as in claim 10, wherein the at least one beam polarization state scrambling system is selected from the group consisting of:
   at least one optical image rotating system which is caused to rotate in use;
   a kaleidoscope;
   a fiber waveguide.

12. A system as in claim 11 in which the at least one optical image rotating system is selected and comprises an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory.

13. A system as in claim 12 in which odd bounce optical image rotating system consists of three reflective elements.

14. A system as in claim 12 in which odd bounce optical image rotating system consists of five reflective elements.

15. A system as in claim 12, in which said at least one beam polarization state scrambling system is an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

16. A system as in claim 10 in which material system investigating system comprises an ellipsometer or polarimeter.

17. A method of compensating detector beam polarization state sensitivity comprising the steps of:
   a) providing a system comprising:
   system for compensating detector beam polarization state sensitivity in a material system investigating system comprising:
   a source of electromagnetic radiation;
   a polarizer;
   a stage for supporting a sample system;
   an analyzer;
   a detector;
   optionally, at least one compensator between said polarizer and analyzer; and
   at least one beam polarization state scrambling system between said analyzer and detector;
   such that in use a beam of electromagnetic radiation provided by said source thereof passes through said polarizer, interacts with a sample system on said stage for supporting a sample system, said beam further passing through any present compensator present between said polarizer and analyzer, then passes through said analyzer and said at least one beam polarization state scrambling system, and then into said detector;

b) causing said source of electromagnetic radiation to direct a beam of electromagnetic radiation through said polarizer, such that it interacts with said sample system on said stage for supporting a sample system, and with any present compensator between said polarizer and analyzer, then passes through said analyzer, through said at least one beam polarization state scrambling system and enters said detector.

18. A method as in claim 17 in which the step of providing a system involves providing said at least one beam polarization state scrambling system in the form of at least one odd bounce optical image rotating system comprising an odd number of at least three reflective elements oriented such that a beam of electromagnetic radiation entered thereinto interacts with each of said at least three reflective elements of said at least one odd bounce optical image rotating system and exits therefrom along a non-deviated non-displaced trajectory.

19. A method as in claim 9, in which said at least one beam polarization state scrambling system is an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

20. A method as in claim 18, in which said at least one beam polarization state scrambling system is an odd bounce optical image rotating system comprising an odd number of at least three reflective elements oriented such that a beam of electromagnetic radiation entered thereinto interacts with each of said at least three reflective elements of said oddbounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

21. An ellipsometer or polarimeter with improved detector performance comprising:
    a source of electromagnetic radiation;
    a polarizer;
    a stage for supporting a sample system;
    an analyzer;
    a detector;
    optionally, at least one compensator between said polarizer and analyzer; and
    at least one beam modifying detector performance improving system between said analyzer and detector;
    such that in use a beam of electromagnetic radiation provided by said source thereof passes through said polarizer and interacts with a sample system on said stage for supporting a sample system, said beam further passing through any present compensator present between said polarizer and analyzer, then passing through said analyzer and said at least one beam modifying detector performance improving system, and then into said detector.

22. An ellipsometer of polarimeter as in claim 21, wherein the at least one beam modifying detector performance improving system is selected from the group consisting of:
    at least one optical image rotating system which is caused to rotate in use;
    a kaleidoscope;
    a fiber waveguide.

23. An ellipsometer of polarimeter as in claim 21 in which the at least one beam modifying detector performance improving system is selected and comprises an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory.

24. An ellipsometer of polarimeter as in claim 23 in which odd bounce optical image rotating system consists of three reflective elements.

25. An ellipsometer of polarimeter as in claim 23 in which odd bounce optical image rotating system consists of five reflective elements.

26. An ellipsometer of polarimeter as in claim 23, in which said at least one beam modifying detector performance improving system is an odd bounce optical image rotating system comprising an odd number of at least three reflective elements oriented such that a beam of electromagnetic radiation entered thereinto interacts with each of said at least three reflective elements of said odd bounce optical image rotating system and exits therefrom along a non-deviated non-displaced trajectory, and in which at least one of said polarizer, analyzer and any at least one compensator between said polarizer and analyzer, is cause to rotate in use, wherein said odd bounce optical image rotating system is, during use, also caused to rotate, all said rotating elements being synchronized and caused to rotate at integer multiples of a selected rotation rate, such that each of said rotating elements simultaneously completes the same, or a different full integer numbers of rotations.

27. A method of improving detector performance in an ellipsometer or polarimeter comprising:
    a) providing an ellipsometer or polarimeter system comprising:
        a source of electromagnetic radiation;
        at least one beam modifying detector performance improving system; and
        a detector;
        such that in use a beam of electromagnetic radiation provided by said source thereof, interacts with said at least one beam modifying detector performance improving system and then enters into said detector;
    b) causing said source of electromagnetic radiation to direct a beam of electromagnetic radiation such taht it passes through said at least one beam modifying detector performance improving system and enters said detector;
    the result being that said detector receives a beam having characteristics which improve results provided thereby.

* * * * *